US00PP14760P2

(12) United States Plant Patent
Zary

(10) Patent No.: US PP14,760 P2
(45) Date of Patent: May 4, 2004

(54) FLORIBUNDA ROSE PLANT NAMED 'JACEIBRE'

(50) Latin Name: *Rosa hybrida*
Varietal Denomination: JACeibre

(75) Inventor: Keith W. Zary, Thousand Oaks, CA (US)

(73) Assignee: Jackson & Perkins Wholesale, Inc., Medford, OH (US)

( * ) Notice: Subject to any disclaimer, the term of this patent is extended or adjusted under 35 U.S.C. 154(b) by 0 days.

(21) Appl. No.: 10/300,573

(22) Filed: Nov. 19, 2002

(51) Int. Cl.[7] ..... A01H 5/00
(52) U.S. Cl. ..... Plt./141
(58) Field of Search ..... Plt./144, 141, 133

*Primary Examiner*—Anne Marie Grunberg
*Assistant Examiner*—June Hwu
(74) *Attorney, Agent, or Firm*—Klarquist Sparkman, LLP

(57) ABSTRACT

Floribunda rose plant having light lavender flower color; moderate citrus fragrance; blooms in large open clusters; dark green, glossy foliage; and compact, well-branched plant habit.

1 Drawing Sheet

Genus and species: *Rosa hybrida.*
Variety denomination: 'JACeibre'.

SUMMARY OF THE INVENTION

The present invention relates to a new and distinct variety of floribunda rose plant named 'JACeibre' which was originated by me by crossing an unnamed seedling with the variety 'TINherb,' (Herbie) U.S. Plant Pat. No. 6,787.

BACKGROUND OF THE INVENTION

The primary objective of this breeding was to produce a new rose variety having the light lavender flower color and vigorous growth of the unnamed lavender floribunda female parent combined with the fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Light lavender flower color;
2. Moderate citrus fragrance;
3. Blooms in large open clusters;
4. Dark green, glossy foliage; and
5. Compact, well-branched plant habit.

Asexual reproduction of this new variety by budding, as performed at Wasco, Calif., shows that the foregoing and all other characteristics and distinctions come true to form and are established and transmitted through succeeding propagations.

COMPARISON WITH PARENTS

The subject variety differs from the female parent in that the latter does not have a fragrance. The female parent also has larger leaves and has fewer flowers in its clusters. The male parent has a darker lavender color, a smaller flower size and smaller plant size.

COMPARISON WITH SIMILAR VARIETY

A similar variety 'JACshok' (U.S. Plant Pat. No. 11,562) has a Red-Purple 66C flower as compared to the Violet-Blue 97D flowers of 'JACeibre.' In addition, 'JACshok' is a larger plant being about 100 cm.×80 cm. as compared to the 80 cm.×50 cm. plant of 'JACeibre.'

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed seedling.
*Pollen parent.*—'TINherb' (U.S. Plant Pat. No. 6,787).

FLOWER

Observations made from plants beginning at 3 years of age grown in a garden environment at Somis and Wasco, Calif. May 2001–May 2002.

Blooming habit: Continuous.
Bud:
*Size.*—About 3 cm long and 1¾ cm in diameter when the petals start to unfurl.
*Form.*—The bud form is pointed ovoid.
*Color.*—When sepals first divide, bud color is Violet-Blue Group 92D often with hints of Yellow-Green Group 144D on the guard petals. When half blown, the upper sides of the petals are close to Violet-Blue Group 97D; and the lower sides of the petals are Violet-Blue Group 97D.

*Sepals.*—Color: Upper surface: Green Group 138B. Lower surface: Yellow-Green Group 144A. Length: 22–30 mm. Width: 7–9 mm. Shape: Subulate. Surface texture: Upper surface: Hoary. Lower surface: Glandular. There are three lightly appendaged sepals. There are two unappendaged sepals with ciliate edges.

*Receptacle.*—Color: Yellow-Green Group 144A. Shape: Funnel. Size: Medium, about 7 mm long×7 mm wide. Surface: Smooth.

*Peduncle.*—Length: Short, averaging about 1½–3 cm. Surface: Hoary. Color: Green Group 143B. Strength: Stiff, erect.

Bloom:

*Size.*—Small. Average open diameter is about 7–9 cm.

*Borne.*—In pyramidal clusters of 3 to 5 blooms.

*Stems.*—Strength: Strong. Average length is about 40–50 cm. Diameter: 6–8 mm.

*Form.*—When first open: High-centered becoming cupped. Permanence: All petals curl.

*Petalage.*—Number of petals under normal conditions: 30–35.

*Color.*—The upper sides of the petals are close to Violet-Blue Group 97D. The reverse sides of the petals are close to Violet-Blue Group 97D. The base of each petal is Purple Group 77D—more prominent on inner petals. The major color on the upper side is Violet-Blue Group 97D.

*Variegations.*—None.

*Discoloration.*—The general tonality at the end of the first-day: Close to Violet-Blue Group 97D. At the end of the third day: Violet-Blue Group 97D. By day five color fades to White Group 155D (per 1966 RHS), then petals drop off.

*Fragrance.*—Moderate, citrus.

Petals:

*Size.*—Length: 16–18 mm. Width: 13–15 mm.

*Texture.*—Thin.

*Surface.*—Smooth.

*Shape.*—Between obovate and obcordate.

*Margin.*—Entire. Apex shape: Obcordate. Base shape: Cuneate.

*Form.*—Tips slightly recurved.

*Arrangement.*—Imbricated.

*Petaloids.*—Size: Length: 4–7 mm. Width: 1–4 mm. Shape: Oblong to Oblanceolate. Number: 5–7. Color: Violet-Blue Group 97D.

*Persistence.*—Petals drop off cleanly before drying.

*Lastingness.*—On the plant: Fair (about 5 days). As a cut flower: Fair (about 7 days).

Reproductive parts:

*Stamens.*—Number: 120–140. Length: 7–10 mm. Anthers: Length: 2 mm. Color: Yellow-White Group 158A. Arrangement: Regular around styles. Filaments: Color: Green-White Group 157D. Length: 5–8 mm. Pollen: Color:. Greyed-Orange Group 168D.

*Pistils.*—Number: 60–80. Length: 6–8 mm. Styles: Color: Greyed-Green Group 192D. Length: 5–7 mm. Stigmas: Color: Yellow-White Group 158B. Length: 1 mm.

*Hips.*—None observed.

PLANT

*Form.*—Bush.

*Growth.*—Vigorous.

*Mature plant.*—Height: 80 cm at two years of age. Width: 50 cm.

*Rootstock.*—Dr. Huey.

Foliage: Number of leaflets on normal mid-stem leaves: 5–7.

*Size.*—Large (10–15 cm long×8–10 cm wide).

*Quantity.*—Normal.

*Color.*—New foliage: Upper side: Greyed-Purple Group 185B. Lower side: Greyed-Purple Group 183A. Old foliage: Upper side: Yellow-Green Group 147A. Lower side: Yellow-Green Group 146B.

Leaflets:

*Size.*—5–6 cm long×3–4 cm wide.

*Shape.*—Ovate.

*Base shape.*—Rounded.

*Apex shape.*—Acuminate.

*Texture.*—Leathery, glossy and lustrous.

*Edge.*—Serrated.

*Serrations.*—Single, small.

*Petiole.*—Color: Yellow-Green group 144C.

*Petiole rachis.*—Color: Yellow-Green Group 144C. Underside: With prickles.

*Auricle shape.*—None present.

*Stipules.*—Glandular. Length about 18–20 mm. Color: Upper surface: Yellow-Green Group 147A. Lower surface: Yellow-Green Group 146B. Shape: Adnate with middle narrowing downwardly. Margin: Comb shaped.

*Disease resistance.*—Resistant to mildew and rust and susceptible to blackspot under normal growing conditions.

*Pest resistance.*—Not tested.

*Vein color.*—Yellow-Green Group 146D.

*Venation pattern.*—Reticulate.

Wood:

*New wood.*—Color: Yellow-Green Group 144B overlaid with a Greyed-Purple Group 183C blush. Bark: Smooth.

*Old wood.*—Color: Green Group 143A. Bark: Smooth.

Prickles:

*Quantity.*—On main canes from base: Few (5 per 10 cm stem). On laterals from main canes: Few (8 per 10 cm stem).

*Form.*—Straight.

*Length.*—9–10 mm..

*Color when young.*—Greyed-Red Group 182A at base, Gryed-Yellow Group 162C on outer two-thirds.

*Color when mature.*—Greyed-Red Group 178C with Greyed-Green Group 194D on tips.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by its light lavender flower color; moderate citrus fragrance; blooms in large open clusters; dark green, glossy foliage; and compact, well-branched plant habit.

* * * * *

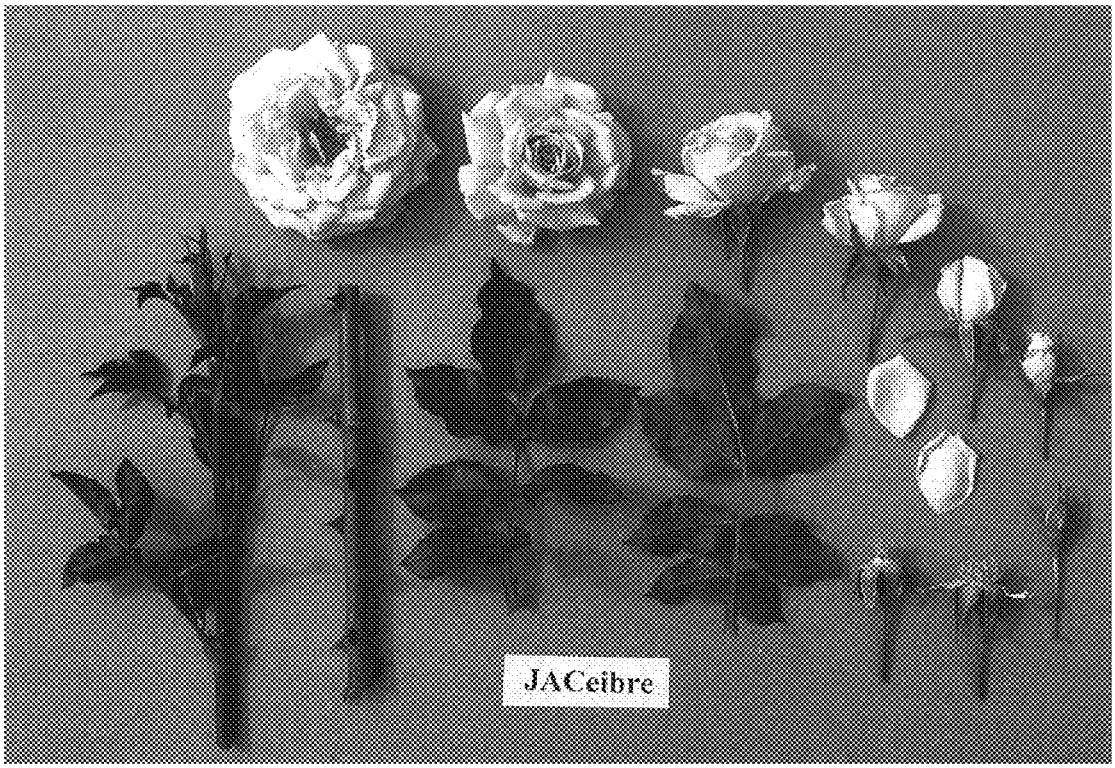
JACeibre